US00PP19526P2

(12) United States Plant Patent
Bunker

(10) Patent No.: US PP19,526 P2
(45) Date of Patent: Dec. 2, 2008

(54) ***CHRYSOCEPHALUM* PLANT NAMED 'FLOCHRDEF'**

(50) Latin Name: *Chrysocephalum apiculatum*
Varietal Denomination: FLOCHRDEF

(75) Inventor: Kerry V. Bunker, Redland Bay (AU)

(73) Assignee: Floreta Intellectual Property Pty. Ltd. (AU)

( * ) Notice: Subject to any disclaimer, the term of this patent is extended or adjusted under 35 U.S.C. 154(b) by 0 days.

(21) Appl. No.: 11/880,705

(22) Filed: Jul. 24, 2007

(51) Int. Cl.
*A01H 5/00* (2006.01)

(52) U.S. Cl. ..... Plt./359

(58) Field of Classification Search ..... Plt./263.1, Plt./359

See application file for complete search history.

*Primary Examiner*—Kent L. Bell
*Assistant Examiner*—June Hwu

(57) ABSTRACT

A new and distinct cultivar of *Chrysocephalum* named FLOCHRDEF, characterized by its grey-green foliage, orange inflorescence color, many flowering shoots per plant, many inflorescences held on long racemes, long flowering period, and its compact plant habit.

1 Drawing Sheet

The present invention relates to a new and distinct cultivar of *Chrysocephalum* plant, botanically known as *Chrysocephalum apiculatum* (formerly *Helichrysum apiculatum*), and referred to by the variety denomination 'FLOCHRDEF'. The species is native to Australia and is known by the common names yellow buttons and common everlasting daisy.

BACKGROUND OF THE INVENTION

The new cultivar is the product of a planned breeding program carried out by the inventor in Redland Bay, Australia in September 2002. The objective of the breeding program was to create new *chrysocephalum* cultivars having a compact plant habit, many flowering shoots, long racemes with many inflorescences, silver-grey foliage, and a long flowering period.

The female or seed parent was unpatented Proprietary Selection 02-47. The female parent is characterized by its open plant habit with spatulate leaves sparsely covered with silver hairs, few short racemes with few inflorescences held in tight clusters, and very short involucral bracts which are yellow in color.

The male or pollen parent is unknown since the pollination was performed in isolation using native insects. Possible male parents are unpatented Proprietary Selection 01 - 11 or unpatented Proprietary Selection 01 - 13. Both of these selections are generally characterized by their open pendulous to upright plant habit, small glossy linear leaves, long weeping flowering stalks with few inflorescences held in loose clusters, and very short involucral bracts that are yellow in color.

The first act of asexual reproduction of the new cultivar was accomplished by vegetative cuttings from the selection in August 2003 in a controlled environment in Redland Bay, Queensland, Australia, by or under the supervision of the inventor. Horticultural examination of controlled flowerings of successive plantings has shown that the unique combination of characteristics of the new cultivar are firmly fixed and are retained through successive generations of asexual reproduction.

The new cultivar has not been observed under all possible environmental conditions. The phenotype may vary significantly with variations in environment such as temperature, light intensity, fertilization levels, and day length without, however, any variance in genotype. The following observations, measurements and comparisons describe plants grown in Redland Bay, Queensland, Australia, under normal commercial growing conditions. The age of the plant described is 40 weeks.

SUMMARY OF THE INVENTION

The following traits have been repeatedly observed and have been determined to be basic characteristics of the new cultivar, which in combination distinguish the new cultivar as being new and distinct:

1. Grey-green foliage
2. Many flowering shoots per plant
3. Many orange inflorescences per raceme
4. Long racemes
5. Long flowering period
6. Compact plant habit The new cultivar differs from the possible male parents described above by its compact upright habit, the presence of silver hairs on the leaves, spatulate leaf shape, upright flowering stems, and a greater number of flowering stems per plant, with many inflorescences per raceme. The new cultivar differs from its female parent by the characteristics of compact plant habit, denser silver hairs on the leaves, greater number of flowering stems, and longer racemes containing many more inflorescences in loose clusters.

Of the many commercial cultivars known to the present inventor, the most similar in comparison to the new cultivar is the cultivar *Chrysocephalum* 'FLOCHRYEL', disclosed in a pending U.S plant patent application. In comparative testing conducted in Redland Bay, Queensland, Australia, plants of the new cultivar differ from plants of the comparison cultivar as described in Table 1:

TABLE 1

| Trait | 'FLOCHRDEF' | 'FLOCHRYEL' |
|---|---|---|
| Silver hairs on leaves | dense | very dense |
| Leaf color | grey-green | silver-grey |
| Inflorescence color | orange | lemon |
| Number of inflorescences per raceme | 12 to 19 | 5 to 11 |
| Number of racemes per plant | very many | many |
| Raceme length | 13 cm | 4 cm |
| Shoot length | 25 cm | 15 cm |

BRIEF DESCRIPTION OF THE PHOTOGRAPHS

The top photograph shows an overall view of a typical flowering plant of the new cultivar, 16 weeks after planting a vegetative cutting.

The bottom photograph shows in detail the capitula on a raceme of the new cultivar.

The photographs show the colors as true as is reasonably possible with colored reproductions of this type. If any differences exist between the photographic color and the color values described below, the values in the detailed description are accurate.

DETAILED BOTANICAL DESCRIPTION

In the following description color references are made to The Royal Horticultural Society Colour Chart. The values are based on plant material 40 weeks old grown in Redland Bay, Queensland, Australia, and the values were taken on approximately May 1, 2007.

Botanical classification: *Chrysocephalum apiculatum* 'FLOCHRDEF'.

*Seed parent*.—Unpatented Proprietary Selection of *Chrysocephalum apiculatum* identified by Code No. 02 - 47.

*Pollen parent*.—Unknown for reasons noted above.

Propagation:

*Type*.—Tip cuttings.

*Time and temperature to initiate roots*.—Summer, about 21 to 28 days at 25 to 30 deg. C in a greenhouse; winter, about 35 to 42 days at 15 to 25 deg. C in a greenhouse.

*Rooting description*.—Fine to fibrous; pale brown in color.

*Rooting habit*.—Freely branching.

Plant description:

*General appearance and form*.—Compact and bushy growth habit; upright and rounded plant form, with long racemes held above the foliage.

*Growth and branching habit*.—Freely branching with lateral branches forming at every node to produce a dense and bushy plant.

*Plant habit*.—Dome shaped, compact, freely branching, vigorous plant.

*Plant height* (*measured from top of soil line*).—25 cm.

*Plant diameter*.—60 cm.

*Time to produce mature plant*.—After rooting, about 12 weeks are required to produce finished flowering plants in 14 cm. pots.

*Plant hardiness*.—Plant will grow and continuously flower in Queensland, Australia.

Branches:

*Number of branches per plant*.—1082 .

*Length*.—7.5 cm.

*Width*.—1.5 cm.

*Internode length*.—About 3.9 mm.

*Orientation*.—Erect.

*Texture*.—Both upper or outer and lower or inner surfaces are moderately pubescent.

*Color*.—195 D.

Foliage description:

*Arrangement*.—Alternate, linear to spatulate, broadly sessile.

*Length*.—2 to 3 cm.

*Width*.—About 7 mm.

*Shape at apex*.—Apiculate.

*Shape at base*.—Attenuate.

*Margin*.—Entire, incurved.

*Color of young foliage*.—Upper surface: 189 B Lower surface: 196 A.

*Color of mature foliage*.—Upper surface: 194 A Lower surface: 194 C. Leaf texture: Upper surface moderately pubescent, lower surface densely pubescent.

Inflorescence description:

*Inflorescence*.—Raceme on long stems; involucral bracts and disc florets develop acropetally on pedicelled capitula that are circular in shape.

*Number of capitula per raceme*.—14 .

*Number of racemes per plant*.—505.

*Diameter of mature capitulum*.—5.8 mm.

*Depth* (*height*) of mature capitulum.—6.0 mm.

*Disc florets*.—Tubular disc florets massed in the center of the receptacle with one to two whorls of filiform florets at the perimeter of the disc.

*Quantity per inflorescence*.—About 70 .

*Shape*.—Tubular with 5 lobes.

*Length*.—About 4.5 mm.

*Diameter at apex*.—Less than 0.5 mm.

*Color of mature discs*.—23 A.

*Natural flowering season*.—Perpetual flowering in Redland Bay, Queensland, Australia.

*Quantity of inflorescences*.—At one time, more than 505 racemes containing more than 7000 flowers and buds per plant.

*Fragrance*.—Sweet musky fragrance.

*Bud*.—Shape: Roughly ovoid. Length: About 4.0 mm. Diameter: About 3.5 mm. Color: 14A.

*Involucral bracts*.—Number per capitulum: 128. Shape: Ligulate, reflexed. Length: About 3.8 mm. Width: About 0.6 mm. Texture: Upper and lower surfaces; smooth, papery, stiff. Color: Underside 17 B, upper side 16 A. Peduncles: Average length 12 cm, surface texture densely pubescent: color 196D.

Reproductive organs:

*Androecium*.—Present only on disc florets, five in number; minute.

*Arrangement*.—Fused anther tube with five long thin linear anthers surrounding the style.

*Anther length*.—Less than 1 mm.

*Anther color*.—Yellow.

*Amount of pollen*.—Moderate.

*Pollen color*.—Yellow.

*Gynoecium*.—One present on both filiform and disc florets; minute.

*Quantity per floret*.—One.

*Style color*.—Yellow-orange.

*Stigma shape*.—Biparted.
*Stigma color*.—Yellow-orange.

Seed:
*Shape*.—Cylindrical.
*Length*.—1 mm.
*Diameter*.—0.5 mm.
*Color*.—Brown.

Disease/pest susceptibility: Plants of the new *Chrysocephalum* have not been observed to be abnormally resistant to pathogens or pests common to *Chrysocephalum*.

Temperature tolerance: Plants of the new cultivar will tolerate temperatures from 0 to 40 degrees C.

Growth retardants: Growth retardants are not necessary to enhance plant performance.

I claim:

1. A new and distinct cultivar of *Chrysocephalum* plant named FLOCHRDEF, as illustrated and described.

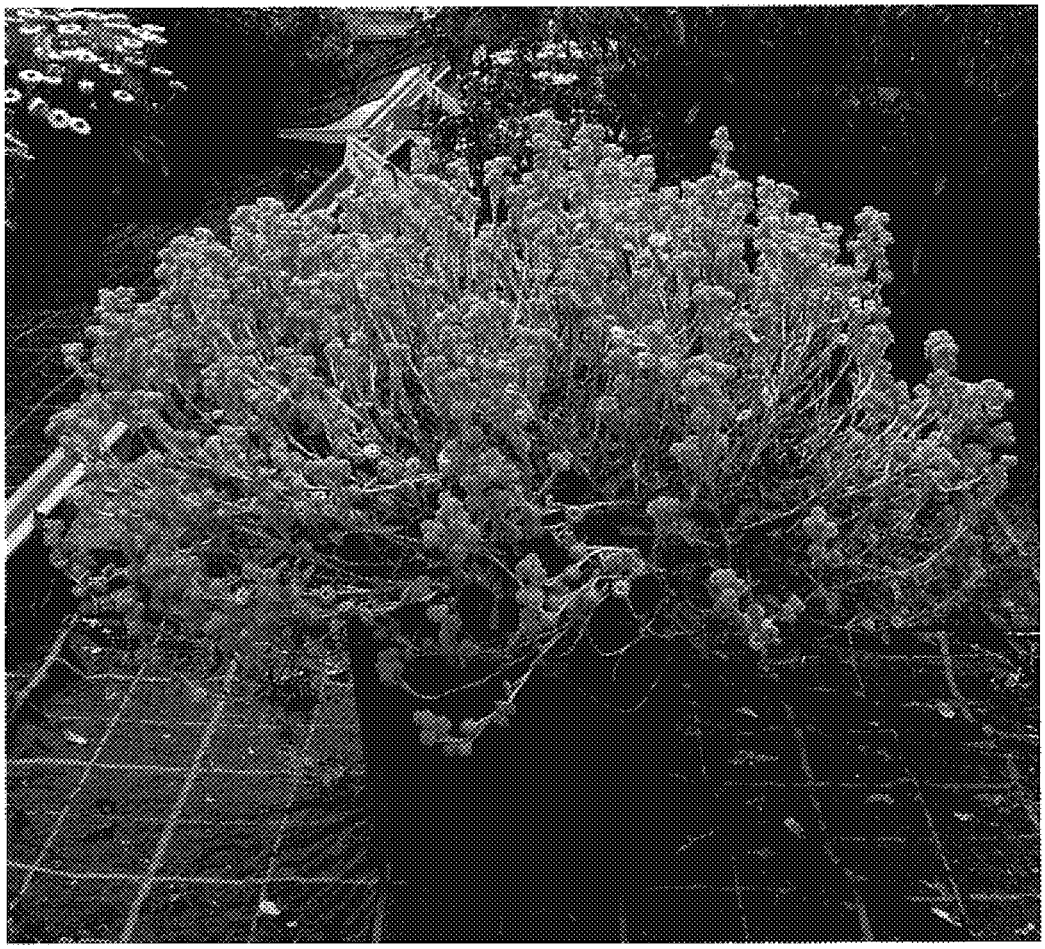
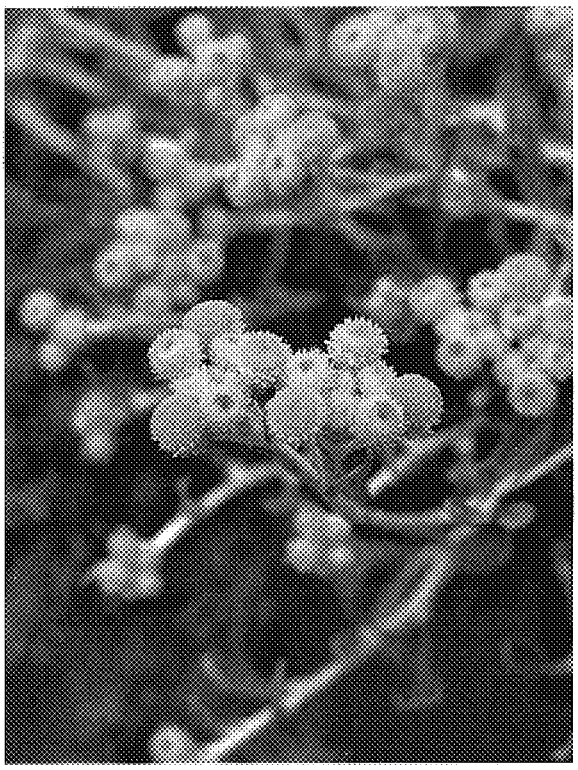

* * * * *